United States Patent
Mitose et al.

[11] Patent Number: 5,951,793
[45] Date of Patent: *Sep. 14, 1999

[54] NI-TI-PD SUPERELASTIC ALLOY MATERIAL, ITS MANUFACTURING METHOD, AND ORTHODONTIC ARCHWIRE MADE OF THIS ALLOY MATERIAL

[75] Inventors: Kengo Mitose; Tatsuhiko Ueki, both of Tokyo, Japan

[73] Assignee: The Furukawa Electric Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/677,299

[22] Filed: Jul. 9, 1996

[30] Foreign Application Priority Data

Jul. 12, 1995 [JP] Japan .................................. 7-199129

[51] Int. Cl.$^6$ ........................................................ C22F 1/10
[52] U.S. Cl. ........................ 148/563; 148/402; 148/421; 148/442; 148/576
[58] Field of Search ...................... 433/20, 21; 148/402, 148/563, 421, 442, 576; 420/580, 581, 582, 583, 587, 588, 441

[56] References Cited

U.S. PATENT DOCUMENTS

| | | | |
|---|---|---|---|
| 4,849,032 | 7/1989 | Kawaguchi | 420/902 |
| 4,865,663 | 9/1989 | Tuominen et al. | 148/402 |
| 5,358,796 | 10/1994 | Nakamura et al. | 148/402 |

FOREIGN PATENT DOCUMENTS

| | | | |
|---|---|---|---|
| 58-161746 | 9/1983 | Japan | 420/444 |

*Primary Examiner*—Melvyn Andrews
*Attorney, Agent, or Firm*—Lorusso & Loud

[57] ABSTRACT

The present invention provides a Ni—Ti—Pd superelastic alloy material of a composition consisting of, by atomic percent, 34 to 49% nickel, 48 to 52% titanium and 3 to 14% palladium. Optionally, in a part of nickel and/or titanium of this alloy is replaced with one or more elements selected from a group of Cr, Fe, Co, V, Mn, B, Cu, Al, Nb, W and Zr such that these elements to be replaced amount to 2% or less in total (by atomic percent), wherein a stress hysteresis between the loading and unloading stresses in the stress-strain curve at temperatures between Af and Af+5° is as small as 50 to 150 MPa. Since the Ni—Ti—Pd superelastic alloy material having the above composition is excellent in hot workability, it can be hot-worked into a wire having a diameter up to the range from 1 to 5 mm and manufactured at a low cost. Then, a final heat-treatment is given to the hot-worked material at a temperature in the range from 300 to 700° C. through a step of final cold-drawing at a reduction ratio in a cross section area of not less than 20%, whereby an excellent superelastic material is obtained, with a stress hysteresis in the range from 50 to 150 MPa, and a residual strain of 0% or close to 0% after unloading, and which can be suitably used for an orthodontic archwire.

7 Claims, 2 Drawing Sheets

(PRIOR ART NiTi ALLOY)

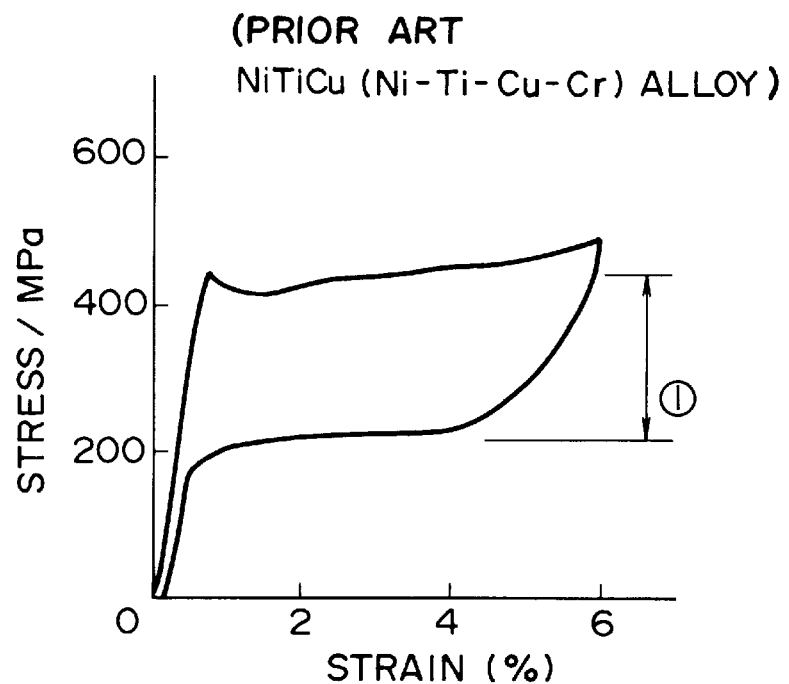

NI-TI-PD SUPERELASTIC ALLOY MATERIAL, ITS MANUFACTURING METHOD, AND ORTHODONTIC ARCHWIRE MADE OF THIS ALLOY MATERIAL

BACKGROUND OF THE INVENTION

1. Field of the Invention

This invention relates to a Ni—Ti—Pd superelastic alloy material which presents a small stress hysteresis, its manufacturing method and an orthodontic archwire made of this alloy material.

2. Description of the Prior Art

In general, a metal material loaded with a stress exceeding its elastic limit results in permanent deformation. However, a certain kind of alloy such as Ni—Ti alloy has a function to go back to its original shape after unloading, even if a stress is loaded to provide such an alloy with a strain close to 10% at a temperature exceeding a reverse Martensite transformation finish (Af) temperature (which will be hereinafter referred to as Af temperature) as shown in FIG. 1. Namely, the Ni—Ti alloy or the like has a superelastic function and is called a superelastic alloy.

Incidentally, FIG. 1 is a typical graph of the stress-strain curve for a superelastic alloy in loading and unloading. Referring to FIG. 1, ① represents a difference between a loading stress $P_1$ in the flat range from a to b and an unloading stress $P_2$ in the flat range from c to d, and this difference is called a stress hysteresis.

The Ni—Ti alloy may be practically used for actuators, toys, pipe coupling or the like by taking advantage of its shape memory properties. In addition, the range of use of the Ni—Ti alloy by taking advantage of its superelastic properties has been recently increasing. Thus, the Ni—Ti alloy has been put into practical use in various fields by taking advantage of stress-strain characteristics similar to rubber. Specifically, the Ni—Ti alloy is frequently used for frames of glasses, wires of brassieres, orthodontic archwires, antennas for portable telephones or the like.

Further, an alloy having a composition adapted for such purposes has been manufactured by adding a small amount of a metal element such as Cr, Fe, Co, V, Mn and B to the Ni—Ti alloy in order to improve the workability and alloy characteristics.

In general, a superelastic alloy material is deformed due to a moderate stress in loading and takes advantage of its high force in unloading. Thus, it is preferable that the superelastic alloy material goes back to its original shape due to a stress which is as close to the stress in loading as possible. Namely, the superelastic alloy material preferably presents a small stress hysteresis. Further, it is necessary that a residual strain should be 0%, or be close to 0% in unloading.

FIG. 2 is a graph of the stress-strain curve for a Ni—Ti superelastic alloy. As is apparent from FIG. 2, a stress hysteresis (shown by ① in FIG. 2) is as large as approximately 300 to 400 MPa, and therefore, there has been a limit in the use of such a Ni—Ti superelastic alloy.

On the other hand, a Ni—Ti—Cu alloy has been developed as a superelastic alloy which presents a small stress hysteresis. FIG. 3 is a graph of the stress-strain curve for the Ni—Ti—Cu superelastic alloy.

It has been found that the stress hysteresis of the Ni—Ti—Cu alloy is reduced as the amount of Cu in the alloy is increased, and that the stress hysteresis in a composition containing, by atomic percent, approximately 10% Cu is reduced down to 100 to 200 MPa and 20% Cu is reduced down to 40 MPa on a laboratory level (S. Miyazaki, I. Shiota, K. Otsuka and H. Tamura. Proc. of MRS Int'l. Mtg on Adv. Mats., Vol. 9 (1989) Page 153, Hiroshi Horikawa and Tatsuhiko Ueki, Advanced Materials '93. V/B: Shape Memory Materials and Hydrides, edited by K. Otsuka et al. Trans. Mat. Res. Soc. Jpn., Volume 18B Page 1113, U.S. Pat. No. 5,044,947). The Ni—Ti—Cu alloy having such a feature is mainly used for orthodontic archwires.

However, the hot workability of the Ni—Ti—Cu superelastic alloy is remarkably reduced as the amount of Cu in the alloy is increased. Thus, an alloy containing a large amount of Cu cannot be manufactured on a factory level. In addition, the stress hysteresis cannot be reduced to only about 160 MPa under the existing circumstances.

Accordingly, the development of a superelastic alloy material which is excellent in workability and presents an extremely small stress hysteresis has been needed. Incidentally, it is necessary for the superelastic alloy material that the residual stress in unloading as described above should show 0% or be close to 0%.

SUMMARY OF THE INVENTION

It is an object of the present invention to provide superelastic alloy materials which present a small stress hysteresis by remedying the problems in the above-mentioned prior art.

Another object of the present invention is to provide a method of manufacturing these alloy materials.

A further object of the present invention is to provide an orthodontic superelastic alloy wire which presents a small stress hysteresis.

The present invention for attaining the above objects has the following features.

Namely, in the first aspect of the present invention, there is provided a Ni—Ti—Cu superelastic alloy material which comprises a composition consisting of, by atomic percent, 34 to 49% nickel (Ni), 48 to 52% titanium (Ti), and 3 to 14% palladium (Pd), wherein a stress hysteresis between the loading and unloading stresses in the stress-strain curve at temperatures between Af and Af+5° is in the range from 50 to 150 MPa.

In the second aspect of the present invention, there is provided a Ni—Ti—Pd superelastic alloy material, which is characterized in that in the Ni—Ti—Pd alloy composition described above, a part of nickel and/or titanium is replaced with one or two or more elements selected from a group consisting of Cr, Fe, Co, V, Mn, B, Cu, Al, Nb, W and Zr such that these elements to be replaced amount to 2% or less (by atomic percent) in total, and a stress hysteresis between the loading and unloading stresses in the stress-strain curve at temperatures between Af and Af+5° is within the range from 50 to 150 MPa.

In the third aspect of the present invention, there is provided a method of manufacturing a Ni—Ti—Pd superelastic alloy material, which comprises the steps of hot-working a slab of a Ni—Ti—Pd alloy having the composition as defined in any of the first and second aspects into a wire having a diameter in the range from 1 to 5 mm, then repeatedly cold-drawing and annealing the hot-worked wire into a wire having a predetermined diameter at need, then annealing the wire having the predetermined diameter, then cold-drawing the annealed wire into a wire having a final finish diameter at a reduction ratio in a cross section area of not less than 20%, and giving a final heat-treatment to the cold-drawn wire at a temperature in the range from 300 to 700° C., whereby a stress hysteresis between the loading and unloading stresses in the stress-strain curve at temperatures between Af and Af+5° is set to be in the range from 50 to 150 MPa.

Further, in the fourth aspect of the present invention, there is provided an orthodontic archwire made of the Ni—Ti—Pd superelastic alloy material as defined in any of the first and second aspects of the present invention.

A detailed description will now be given of the present invention.

The Ni—Ti—Pd superelastic alloy material according to the present invention is provided as a superelastic alloy material which presents a stress hysteresis smaller than that of the conventional Ni—Ti—Cu alloy material and is excellent in hot workability. A value of the stress hysteresis, i.e. difference between the loading and unloading stresses in the stress-strain curve for this alloy material at a temperature exceeding the Af temperature, is in the range from 50 to 150 MPa. Thus, the stress hysteresis of the Ni—Ti—Pd alloy material of the present invention is extremely smaller than those of Ni—Ti and Ni—Ti—Cu alloy materials, and its behavior in unloading is reverse of that in loading.

Incidentally, FIGS. 2, 3 and 4 show typical graphs of the stress-strain curves for Ni—Ti, Ni—Ti—Cu and Ni—Ti—Pd superelastic alloy materials in loading and unloading at a temperature exceeding the Af temperature, respectively.

In the Ni—Ti—Pd superelastic alloy material as the first aspect of the present invention, the amount of palladium (Pd) is set to be in the range from 3 to 14% (by atomic percent) for the following reasons. Namely, when the amount of palladium is less than 3%, an effect on reduction of the stress hysteresis will not be produced. On the other hand, when the amount of palladium exceeds 14%, the cold workability is degraded, and therefore, it is of no practical use.

In addition, the amount of nickel and that of titanium are set to be in the range from 34 to 49% and in the range from 48 to 52% (by atomic percent) for the following reasons. Namely, if the amount of nickel and that of titanium are respectively outside the above range, the workability is degraded and residual strain remains after unloading.

Accordingly, in the Ni—Ti—Pd superelastic alloy material of the present invention, the alloy composition consisting of, by atomic percent, 50% titanium, 41 to 45% nickel and 5 to 9% palladium is the most preferable alloy composition, which will not only reduce the stress hysteresis but also obtain the satisfactory hot workability.

Further, in the superelastic alloy material as the second aspect of the present invention, a part of nickel and/or titanium in the Ni—Ti—Pd alloy composition described above is replaced with one or two or more elements selected from a group consisting of Cr, Fe, Co, V, Mn, B, Cu, Al, Nb, W and Zr such that these elements to be replaced amount to 2% or less (by atomic percent) for the following reasons. Namely, such replacement makes it possible to improve the alloy characteristics such as Af temperature and the workability of the alloy material, and to vary the alloy characteristics so as to be fit for the purpose.

According to the present invention in the first and second aspects, it is a matter of course that the stress hysteresis between the loading and unloading stresses in the stress-strain curve at temperatures between Af and Af+5° is set to be in the range from 50 to 150 MPa. The stress hysteresis as small as the range from 50 to 150 MPa obtained in the alloy material of the present invention is preferable from the viewpoint of practical use. Incidentally, in the superelastic alloy material as defined in the first and second aspects of the present invention, a residual strain of not more than 0.5% is shown after unloading the stress which is loaded to provide such the superelastic alloy material for a strain up to 8%, as is apparent from examples 3 and 4 which will be described later.

In the third aspect of the present invention, there is provided the method of manufacturing the Ni—Ti—Pd superelastic alloy material. In the case of manufacturing this alloy material, the slab having the above alloy composition is firstly hot-worked into a wire having a diameter in the range from 1 to 5 mm. Since the Ni—Ti—Pd superelastic alloy material is excellent in hot workability, the slab is hot-worked into the wire having the diameter as small as 1 to 5 mm as described above, and the cost of manufacture is sharply reduced.

Incidentally, with respect to the sectional shape of the wire having the diameter in the range from 1 to 5 mm, a wire having a circular sectional shape is easily manufactured and is in common use. Alternately, a wire may have an elliptical or square sectional shape. In this case, the maximum diameter of the elliptical or square wire should be in the range from 1 to 5 mm as the wire diameter.

The wire hot-worked in this manner is repeatedly cold-drawn and annealed, as needed, to form a wire having a predetermined diameter, which is then annealed. Subsequently, the annealed wire having the predetermined diameter is cold-drawn into a wire having a final finish diameter at a reduction ratio in a cross section area of not less than 20%. Further, a final heat-treatment is given to the cold-drawn wire having the final finish diameter at a temperature in the range from 300 to 700° C.

Incidentally, although not restricted, it is preferable that the alloy material of the present invention is hot-worked at a temperature in the range from 700 to 900° C., and annealed at a temperature in the range from 600 to 800° C.

The slab is hot-worked into the wire having the diameter in the range from 1 to 5 mm as described above in order to do away with or reduce the steps of cold-drawing and annealing along the manufacturing line as much as possible. It is preferable that the slab is hot-worked into a wire having a diameter close to the final finish diameter.

As described above, for instance, in case a wire having the final finish diameter of 1 mm is required and the diameter of the hot-worked wire is 1.2 mm, the hot-worked wire having the diameter of 1.2 mm is cold-drawn to a diameter of 1 mm (a cold reduction ratio in a cross section area of approximately 30%) without the steps of cold-drawing and annealing along the manufacturing line. In another case the wire having the final finish diameter of 1 mm is required and the diameter of the hot-worked wire is 3.0 mm, the hot-worked wire having the diameter of 3.0 mm is repeatedly cold-drawn and annealed to form a wire having a diameter of 1.2 mm, which is then annealed. Subsequently, the annealed wire is cold-drawn into a wire having a diameter to 1 mm (a final cold reduction ratio in a cross section area of approximately 30%).

The wire cold-drawn at the reduction ratio in a cross section area of not less than 20% as described above is finally heat-treated at a temperature in the range from 300 to 700° C. The reason why the wire is cold-drawn at the above reduction ratio and then heat-treated in this manner is that satisfactory superelastic properties are obtained in the above range of the reduction ratio and that of the temperature for heat treatment without any residual strain after unloading.

Incidentally, the final sectional shape of the wire may be circular, elliptical or square. Further, although the reduction ratio in a cross section area of not less than 20% is required in the cold-drawing, its upper limit is approximately 60%. When the reduction ratio exceeds 60%, there is a fear of the occurrence of breakage.

In the fourth aspect of the present invention, there is provided the orthodontic archwire made of the Ni—Ti—Pd superelastic alloy material having the alloy composition as defined in any of the first and second aspects of the present invention, wherein the stress hysteresis between the loading and unloading stresses in the stress-strain curve at temperatures between Af and Af+5° is in the range from 50 to 150 MPa.

When the superelastic alloy material is used for the orthodontic archwire, it is desired that a certain amount of tensile force should be applied in working (loading) to attach the wire to the teeth, and that a tensile force should be as high as possible in unloading to move the teeth after attaching the wire to the teeth, namely, the stress hysteresis should be small. Thus, it can be said that the Ni—Ti—Pd superelastic alloy material of the present invention has characteristics, which have not been found until now, suitable for an orthodontic archwire, since its stress hysteresis is as small as 50 to 150 MPa.

BRIEF DESCRIPTION OF THE DRAWINGS

The foregoing and other objects and features of the invention will become apparent from the following description of preferred embodiments of the invention with reference to the accompanying drawings, in which:

FIG. 3 is a graph showing the stress-strain curve for a Ni—Ti—Cu superelastic alloy (Ni—Ti—Cu—Cr alloy) in loading and unloading, in which ① represents a stress hysteresis; and FIG. 4 is a graph showing the stress-strain curve for a Ni—Ti—Pd superelastic alloy according to the present invention in loading and unloading, in which ① represents a stress hysteresis.

DESCRIPTION OF THE PREFERRED EMBODIMENTS

Example 1

Figure 1:
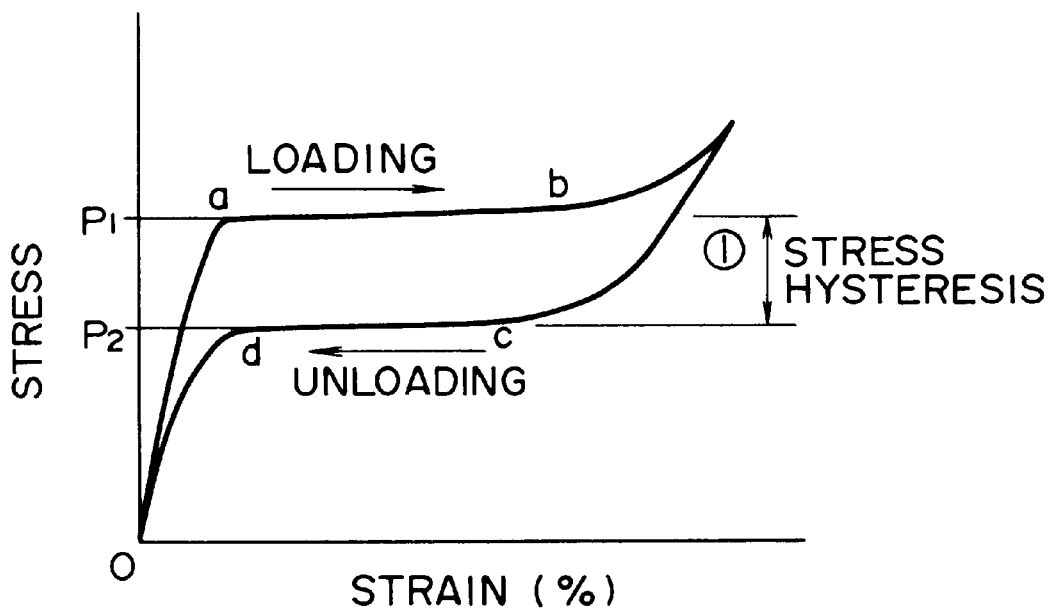
FIG. 1 is a typical graph showing the stress-strain curve for a superelastic alloy in loading and unloading, in which ① represents a stress hysteresis.
Figure 2:
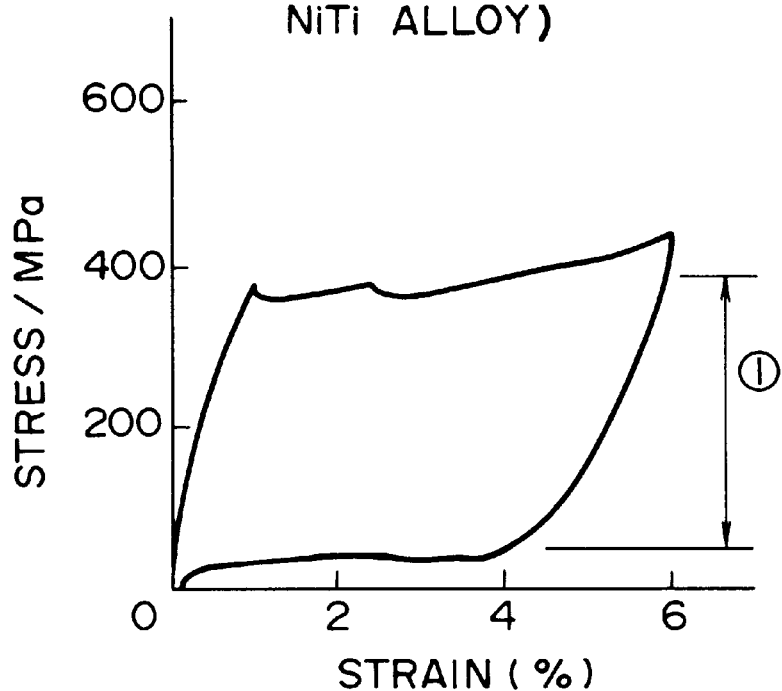
FIG. 2 is a graph showing the stress-strain curve for a Ni—Ti superelastic alloy in loading and unloading, in which ① represents a stress hysteresis.

Superelastic alloy materials having the composition shown in Table 1 were manufactured on an experimental basis as an example of the present invention and a comparative example. Namely, each alloy composition shown in Table 1 was melted and cast into a slab, which was then hot-rolled at a temperature in the range from 750 to 850° C. into a wire having a diameter of 3 mm. Then, this hot-rolled wire was repeatedly cold-drawn and annealed into a wire having a predetermined small diameter (about 1.2 mm), which was then annealed (at a temperature of 700° C.). The annealed wire was cold-drawn at a reduction ratio in a cross section area of 30% into a wire having a diameter of 1 mm. Thereafter, a final heat-treatment was given to this cold-drawn wire for 60 minutes at a temperature of 400° C. to manufacture a test material. Incidentally, in the hot working, Ni—Ti—Pd alloy materials (Nos. 1 to 10 in Table 1) were excellent without any cracks the surface of the wire. On the other hand, Ni—Ti—Cu alloy materials (Nos. 11 and 12 in Table 1) caused cracks on the surface of the wire. Thus, with respect to the Ni—Ti—Cu alloy materials, the satisfactory portions of the hot-worked material were used for the following working of the wire, and a test material having a diameter of 1 mm was manufactured. The stress-strain curves for these wires in loading and unloading were obtained.

A test was made to unload a stress which had been loaded so as to provide the test material with a strain up to 4% with the test temperature was set to be in the range of temperatures between Af and Af+5° of each alloy. The difference (stress hysteresis) between loading and unloading stresses was found from the stress-strain curve, and the results obtained are shown in Table 1.

In addition, Af temperature (reverse Martensite transformation finish temperature) of each alloy was measured by means of thermal analysis, and the results obtained are shown in Table 1. The unloading stresses (MPa) under the strain of 2% are also shown in Table 1 for reference.

TABLE 1

|  | No | Alloy composition (at %) | Af temperature (°C.) | Hot workability | Unloading stress under strain of 2% (MPa) | Stress hysteresis (MPa) |
|---|---|---|---|---|---|---|
| Example of present invention | 1 | $Ni_{46.5}Ti_{49.5}Pd_4$ | 5 | o | 240 | 137 |
|  | 2 | $Ni_{42.5}Ti_{50}Pd_{7.5}$ | 25 | o | 340 | 95 |
|  | 3 | $Ni_{40.5}Ti_{49.5}Pd_{10}$ | −20 | o | 340 | 54 |
|  | 4 | $Ni_{35}Ti_{51}Pd_{14}$ | 60 | o | 170 | 127 |
|  | 5 | $Ni_{47}Ti_{49.5}Pd_3Cr_{0.5}$ | 5 | o | 220 | 148 |
|  | 6 | $Ni_{36}Ti_{49}Pd_{13}Fe_2$ | −30 | o | 200 | 103 |
|  | 7 | $Ni_{42}Ti_{50}Pd_{7.5}Co_{0.5}$ | 15 | o | 350 | 82 |
|  | 8 | $Ni_{38}Ti_{49.5}Pd_{12}V_{0.5}$ | 30 | o | 180 | 106 |
| Comparative Example | 9 | $Ni_{47.5}Ti_{50}Pd_{2.5}$ | 55 | o | 205 | 263 |
|  | 10 | $Ni_{36}Ti_{49}P_{15}$ | −50 | o | 165 | 170 |
|  | 11 | $Ni_{43.5}Ti_{49.5}Cu_7$ | 25 | x | 380 | 236 |
|  | 12 | $Ni_{40}Ti_{50}Cu_{10}$ | 60 | x | 395 | 172 |

Note) In Table, o represents that no crack is produced on the surface of the wire in hot working. x represents that the surface of the wire is cracked in hot working.

As is apparent from Table 1, with respect to the Ni—Ti—Cu alloys of Nos. 11 and 12, cracks were produced in hot working, and the yield was remarkably reduced. The Ni—Ti—Cu alloy of No. 12 presented a stress hysteresis of 172 MPa and showed relatively satisfactory characteristics. However, considering the hot workability, it is difficult to manufacture the Ni—Ti—Cu alloy on a factory level, and further reduction of the stress hysteresis is not expected in the Ni—Ti—Cu alloy.

On the other hand, the Ni—Ti—Pd alloys of Nos. 1 to 10 were excellent in hot workability. Namely, each of these Ni—Ti—Pd alloys could be hot-worked into a wire having a diameter to 3 mm without producing any cracks on the surface of the wire in hot rolling, differently from the Ni—Ti—Cu alloy materials. The Ni—Ti—Pd alloys of Nos. 9 and 10, the comparative examples, were excellent in workability, but presented a large stress hysteresis. Thus, as a result, the Ni—Ti—Pd alloys of Nos. 9 and 10 are not superior in characteristics to the conventional Ni—Ti—Cu alloys. On the other hand, the Ni—Ti—Pd alloys of Nos. 1 to 8 as the example of the present invention were excellent in hot workability, and the stress hysteresis was as small as 50 to 150 MPa, which were not only reduced down to ½ to 9/10 in comparison with the stress hysteresis of the Ni—Ti—Cu alloys, but also exhibited excellent formability in hot-working.

Further, the alloys of Nos. 5 to 8 were prepared by replacing a part of nickel and titanium in the Ni—Ti—Pd alloy with the elements Cr, Fe, Co and V, respectively. When the amount of Cr, Fe, Co or V exceeds 2% (by atomic percent) in total, the workability was remarkably reduced, and therefore, its working was impossible. Further, as long as the elements to be replaced amount to 2% or less (by atomic percent) in total, although two or more elements are added in the alloy, it is possible to manufacture a Ni—Ti—Pd superelastic alloy which is excellent in hot workability and presents a stress hysteresis as small as 80 to 150 MPa.

Example 2

Table 2 shows an example of the present invention and a comparative example in case of varying the temperature for final heat-treatment after cold-working.

Specifically, the alloy of No. 2 shown in Table 1 was cold-drawn at a reduction ratio in a cross section area of 30% into a wire having the diameter of 1 mm on an experimental basis, similarly to the example 1. Subsequently, a final heat-treatment was given to this cold-drawn wire on conditions shown in Table 2.

The wire thus manufactured was tested similarly to the example 1, except that a stress was loaded to provide this wire with a strain up to 8%. Then, the stress-strain curves in loading and unloading were obtained. The residual strain (%) after unloading and the stress hysteresis (MPa) in this case were found, and the results obtained are shown in Table 2.

TABLE 2

| | Heat-treatment temperature (°C.) | Time (min.) | Residual strain (%) | Stress hysteresis (MPa) |
|---|---|---|---|---|
| Comparative example | 250 | 60 | Breakage | — |

TABLE 2-continued

| | Heat-treatment temperature (°C.) | Time (min.) | Residual strain (%) | Stress hysteresis (MPa) |
|---|---|---|---|---|
| Example of present invention | 300 | 30 | 0.2 | 83 |
| | 450 | 60 | 0.0 | 95 |
| | 700 | 5 | 0.1 | 93 |
| Comparative example | 750 | 5 | 1.5 | 90 |

As is apparent from Table 2, the material heat-treated at the temperature of 250° C. was broken under the strain of 7%. In addition, the material heat-treated at the temperature of 750° C. is not suitable for a super-elastic alloy material, since the high residual strain after unloading is found. On the other hand, it can be seen that the materials heat-treated at temperature in the range from 300 to 700° C. result in excellent superelastic alloy materials, since the residual strain is approximately 0% and the stress hysteresis is as small as 80 to 100 MPa.

Example 3

The alloy having the composition shown in No. 3 of Table 1 was hot-worked into a wire having a diameter to 3 mm, similarly to the example 1. The wire thus hot-worked was then repeatedly cold-drawn and annealed into a wire having a predetermined small diameter, which was then annealed (at the temperature of 700° C.). Then, the annealed wire was drawn at a reduction ratio in a cross section area shown in Table 3 to manufacture a wire having a diameter of 1 mm on an experimental basis. Thereafter, a final heat-treatment was given to this wire for 60 minutes at the temperature of 400° C.

The wire thus manufactured was tested similarly to the example 1, except that a stress was loaded to provide this wire with a strain up to 8%, and the stress-strain curves in loading and unloading were obtained. The residual strain (%) after unloading and the stress hysteresis (MPa) in this case were found, and the results obtained are also shown in Table 3.

TABLE 3

| | Reduction ratio in cross section area (%) | Residual strain (%) | Stress hysteresis (MPa |
|---|---|---|---|
| Comparative example | 0 | 2.0 | 113 |
| | 10 | 1.5 | 104 |
| Example of present invention | 20 | 0.3 | 93 |
| | 30 | 0.0 | 95 |
| | 50 | 0.2 | 85 |

As is apparent from Table 3, with respect to all samples worked at the reduction ratio in a cross section area of 0% and 10%, high residual strain is found. On the other hand, with respect to those samples worked at the reduction ratio in a cross section area of not less than 20%, the residual strain is as small as approximately 0%. Accordingly, it is possible to provide an excellent superelastic alloy, in which the residual strain is approximately 0%, and the stress hysteresis is in the range from approximately 80 to 100 MPa at the reduction ratio in a cross section area of not less than 20%.

Example 4

The following test was made on the assumption that the alloy material of the present invention is used as an orthodontic archwire.

A slab having an alloy composition shown in Table 4 was hot-worked into a wire having a diameter of 3 mm. Then, this hot-worked wire was repeatedly cold-drawn and annealed into a wire having a diameter of 0.56 mm, which was then annealed at the temperature of 700° C. Then, the annealed wire was finally cold-drawn at the reduction ratio in a cross section area of 35% into a wire having a diameter of 0.45 mm. Thereafter, a final heat treatment was given to the finally cold-drawn wire under the conditions shown in Table 4 to provide an orthodontic archwire.

The orthodontic archwire thus manufactured was tested to obtain the stress-strain curves for loading and unloading. The stress hysteresis (MPa) was obtained by unloading a stress which has been loaded to provide this archwire with a stress up to 8%, with the test temperature set to 30° C.

The alloy composition, the temperature for heat treatment and the stress hysteresis in this test are shown in Table 4.

TABLE 4

|  | Alloy composition (at %) | Af temperature (°C.) | Heat treatment | Unloading stress under strain of 2% (MPa) | Stress hysteresis (MPa) |
| --- | --- | --- | --- | --- | --- |
| Example of present invention | $Ni_{42.5}Ti_{50}Pd_{7.5}$ | 30 | 500° C. | 190 | 130 |
| Comparative example | $Ni_{44.5}Ti_{50}Cu_{5.0}Cr_{0.5}$ | 30 | 400° C. | 200 | 175 |

With respect to alloys of the examples of both the present invention and the comparative examples, the residual strain after unloading was as small as 0.2% or less, and satisfactory superelastic characteristics were obtained. In addition, while the stress hysteresis of a $Ni_{44.5}$ $Ti_{50}$ $Cu_{5.0}$ $Cr_{0.5}$ alloy material as the comparative example was 175 MPa, the stress hysteresis of a $Ni_{42.5}$ $Ti_{50}$ $Pd_{7.5}$ alloy material as the example of the present invention was 130 MPa, which was approximately three quarters that of the comparative example.

As is apparent from the results of this test, in the case of the superelastic alloy material of the present invention used as a orthodontic archwire, the following effects are obtained. Namely, in case of attaching the wire to the teeth, the wire can be fastened to the teeth by a tensile force which is as small as possible. In addition, the teeth can be moved by a force which is as high as possible.

As described in the foregoing, the present invention provides the Ni—Ti—Pd superelastic alloy material, which comprises a composition consisting of, by atomic percent, 34 to 49% nickel, 48 to 52% titanium and 3 to 14% palladium, or the Ni—Ti—Pd superelastic alloy material, which is characterized in that a part of nickel and/or titanium of this alloy is replaced with one or more elements selected from a group consisting of Cr, Fe, Co, V, Mn, B, Cu, Al, Nb, W and Zr such that the elements to be replaced amount to 2% or less (by atomic percent) in total, wherein a stress hysteresis is as small as 50 to 150 MPa. Since the Ni—Ti—Pd superelastic alloy material having the above composition is excellent in hot workability, it can be hot-worked into a wire having a small diameter up to the range from 1 to 5 mm, and also can be manufactured at a low cost. Then, the final cold-drawing is given to the hot-worked wire at the reduction ratio in a cross section area of not less than 20%, and thereafter, the final heat-treatment is given to the finally cold-drawn wire at a temperature in the range from 300 to 700° C., whereby an excellent superelastic alloy material is provided, which presents a stress hysteresis in the range from 50 to 150 MPa and a residual strain of 0% or close to 0% after unloading.

Further, when the superelastic alloy material of the present invention is used as an orthodontic archwire, excellent characteristics can be obtained in attaching the wire to the teeth and in treatment.

What is claimed is:

1. A Ni—Ti—Pd superelastic alloy composition consisting of, by atomic percent, 34 to 49% nickel (Ni), 48 to 52% titanium (Ti) and 3 to 14% palladium (Pd);
    wherein said alloy has a stress hysteresis, between the loading and unloading stresses in the stress-strain curve at temperatures between Af and Af+5°, in the range from 50 to 150 MPa and a residual strain of 0.5% or less.

2. A Ni—Ti—Pd superelastic alloy composition consisting of, by atomic percent of the alloy composition, 34 to 49% Ni, 48 to 52% Ti, 3 to 14% Pd and 0 to 2% of one or more elements selected from the group consisting of Cr, Fe, Co, V, Mn, B, Cu, Al, Nb, W and Zr replacing a part of said Ni and/or said Ti, said alloy composition having a stress hysteresis difference, between the loading and unloading stresses in stress-strain curves at temperatures between Af and Af+5°, in a range from 50 to 150 MPa and a residual strain of 0.5% or less.

3. A method of manufacturing a Ni—Ti—Pd superelastic alloy material, comprising the steps of:

hot-working a slab having an alloy composition according to claim 1 into a wire having a diameter in the range from 1 to 5 mm;

then repeatedly cold-drawing and annealing the hot-worked wire to form a wire having a predetermined diameter;

then annealing the wire having the predetermined diameter;

subsequently cold-drawing the annealed wire into a wire having a final finish diameter at a reduction ratio, in cross-sectional area, of not less than 20%;

then heat-treating the cold-drawn wire at a temperature in the range from 300 to 700° C. to impart the wire with a stress hysteresis, between the loading and unloading stresses in the stress-strain curve at temperatures between Af and Af+5°, in a range from 50 to 150 MPa and a residual strain of 0.5% or less.

4. An orthodontic archwire, comprising:
    the Ni—Ti—Pd superelastic alloy composition according to claim 1.

5. An orthodontic archwire, comprising:
    the Ni—Ti—Pd superelastic alloy composition according to claim 2.

6. An orthodontic archwire according to claim 4 produced by a method comprising the steps of:

hot-working a slab having said alloy composition into a wire having a diameter in the range from 1 to 5 mm;

then repeatedly cold-drawing and annealing the hot-worked wire to form a wire having a predetermined diameter;

then annealing the wire having the predetermined diameter;

subsequently cold-drawing the annealed wire into a wire having a final finish diameter at a reduction ratio, in cross-sectional area, of not less than 20%;

then heat-treating the cold-drawn wire at a temperature in the range from 300 to 700° C. to produce a wire with a stress hysteresis, between the loading and unloading stresses in the stress-strain curve at temperatures between Af and Af+5°, in a range from 50 to 150 MPa.

7. An orthodontic archwire according to claim 5 produced by a method comprising the steps of:

hot-working a slab having said alloy composition into a wire having a diameter in the range from 1 to 5 mm;

then repeatedly cold-drawing and annealing the hot-worked wire to form a wire having a predetermined diameter;

then annealing the wire having the predetermined diameter;

subsequently cold-drawing the annealed wire into a wire having a final finish diameter at a reduction ratio, in cross-sectional area, of not less than 20%;

then heat-treating the cold-drawn wire at a temperature in the range from 300 to 700° C. to produce a wire with a stress hysteresis, between the loading and unloading stresses in the stress-strain curve at temperatures between Af and Af+5°, in a range from 50 to 150 MPa.

* * * * *

UNITED STATES PATENT AND TRADEMARK OFFICE
CERTIFICATE OF CORRECTION

PATENT NO. : 5,951,793
DATED : July 9, 1996
INVENTOR(S) : MITOSE et al.

It is certified that error appears in the above-indentified patent and that said Letters Patent is hereby corrected as shown below:

IN THE ABSTRACT:

Line 4, delete "in".

IN THE SPECIFICATION:

Col. 3, line 23, delete "reverse" and insert –reversed--.

Col. 4, line 26, after "to form" insert –into--.

In Table 1, the Alloy Composition No. for Comparative example 10 listed as "P$_{15}$" should read –Pd$_{15}$--.

Signed and Sealed this

Seventeenth Day of April, 2001

Attest:

NICHOLAS P. GODICI

*Attesting Officer*   *Acting Director of the United States Patent and Trademark Office*